United States Patent
Anderson

(10) Patent No.: US 7,368,135 B1
(45) Date of Patent: May 6, 2008

(54) HERBAL HEALING OIL

(76) Inventor: Linda A. Anderson, 976 Rockbridge Rd., Troutdale, VA (US) 24378

( * ) Notice: Subject to any disclaimer, the term of this patent is extended or adjusted under 35 U.S.C. 154(b) by 40 days.

(21) Appl. No.: 11/491,581

(22) Filed: Jul. 24, 2006

(51) Int. Cl.
*A01N 65/00* (2006.01)

(52) U.S. Cl. .................................................. 424/725

(58) Field of Classification Search .................... None
See application file for complete search history.

(56) References Cited

U.S. PATENT DOCUMENTS

| | | | |
|---|---|---|---|
| 5,032,400 | A | 7/1991 | Wiersum et al. |
| 5,455,033 | A | 10/1995 | Silverman et al. |
| 5,958,397 | A * | 9/1999 | Smerbeck et al. ....... 424/78.03 |
| 5,958,418 | A | 9/1999 | Johnson Prillerman |
| 5,998,335 | A | 12/1999 | Selga et al. |
| 6,146,639 | A | 11/2000 | Merich |
| 6,383,495 | B1 | 5/2002 | Ramakrishna et al. |
| 6,436,150 | B2 | 8/2002 | Watanabe et al. |
| 6,541,045 | B1 | 4/2003 | Charters et al. |
| 6,579,543 | B1 * | 6/2003 | McClung ................... 424/728 |
| 6,582,736 | B2 | 6/2003 | Quezada |
| 6,752,838 | B2 | 6/2004 | Watanabe et al. |

\* cited by examiner

*Primary Examiner*—Michael Meller
*Assistant Examiner*—Qiuwen Mi
(74) *Attorney, Agent, or Firm*—Robert C. Montgomery

(57) ABSTRACT

The invention as presently conceived discloses a chemical formula for the composition of a liquid topical analgesic. It is produced from a unique blend of herbal essential oils and plant- and/or vegetable-derived oils. Although the precise proportions and method of mixture are held in confidence, it comprises at least olive oil, castor oil, grapeseed oil, almond oil, apricot kernel oil, Vitamin E, various herbal essential oils, and a stabilizer. Such essential oils may include eucalyptus (*Eucalyptus globulus*, among others), lavender (*Lavandula angustifolia*), tea tree (*Melaleuca alternifloria*), ginger (*Zingiber officinale*), lemongrass (*Cymbopogon citratus*, among others), red thyme (*Thymus vulgaris*), sweet birch, (*Betula lenta*) and ylang ylang (*Cananga odorata*). Alternate and additional essential oils or plant- and/or vegetable-derived oils are anticipated to be used as well. When produced, the mixture would be bottled and promoted to the public to be used as a topical rubbing compound for the skin or for use in a soaking bath. It will reduce pain from sore muscles, bruised ligaments and tendons, lower back pain, arthritis and other similar ailments associated with common aches and pains.

1 Claim, No Drawings

HERBAL HEALING OIL

RELATED APPLICATIONS

The present invention was first described in Disclosure Document No. 587,875 filed on Oct. 12, 2005.

FIELD OF THE INVENTION

The present invention relates to a formulaic composition of a liquid topical analgesic produced from a unique blend of herbs and essential oils that, when applied to the skin, will alleviate skin problems and reduce the discomfort associated with common aches and pains.

BACKGROUND OF THE INVENTION

Many people suffer from pain that can be derived from a number of sources. Some people suffer from ongoing pain that began as a result of a previous injury that never completely heals or is easily aggravated. Others suffer from pain that stems from the aggregation of years of improper posture and insufficient, or complete lack of, exercise. Finally, others suffer from pain that occurs as a result of a recent stress such as heavy lifting, repeated muscle use, an intense workout or the like. Regardless of the pain's origin, relieving it is essential to a person's general health and well being. Various creams and balms have been used with varying results. Also, the application of heat, such as that obtained through the use of a heating pad, provides relief for some people. However, there are still a great number of people who continue to suffer. Accordingly, there is a need for a means by which almost anyone can obtain relief from skin problems and pain from sore muscles, bruised ligaments and tendons, lower back pain, arthritis and other similar ailments associated with common aches and pains through the use of an all-natural, topical analgesic produced from a mixture of various all-natural plant and vegetable oils. The development of the invention herein disclosed fulfills this need.

Several attempts have been made in the past to provide relief from chronic and acute pain with all-natural products in an over-the-counter composition. U.S. Pat. No. 5,958,418 in the name of Johnson Prillerman discloses an external herbal composition for treating muscle aches and joint pain. This composition consists of an aqueous solution of effective amounts of various herbal essential oils.

U.S. Pat. No. 6,383,495 issued in the name of Ramakrishna et al. provides for an herbal formulation useful for the treatment of skin disorders consisting of plant extracts with conventional additives.

U.S. Pat. No. 6,541,045 issued in the name of Charters et al. describes an herbal composition and method for combating inflammation, comprising mainly Japanese knotweed, Devil's claw, grapeskin, and syzygium.

U.S. Pat. Nos. 6,752,838 and 6,436,150, both issued in the name of Watanabe et al., disclose a fabric protectant against pests comprising various known compounds noxious to fabric-related pests.

U.S. Pat. No. 5,998,335 issued in the name of Selga et al. describes an herbicidal composition and method, consisting essentially of a combination of pine oil, tea tree oil, and eucalyptus oil.

U.S. Pat. No. 5,455,033 issued in the name of Silverman et al. describes a medicinal composition for treatment of inflammation, consisting of essential plant oils, a local anesthetic, and soothing ingredients particularly suited for the treatment of genital ailments.

U.S. Pat. No. 6,582,736 issued in the name of Quezada describes a therapeutic oil composition, method of producing, and method of applying such a composition. The Quezada composition may or may not be applied topically with an oil-based carrier.

U.S. Pat. No. 6,146,639 issued in the name of Merich discloses an arthritis, muscle pain, and dry skin remedy mainly consisting of witch hazel, olive oil, and rubbing alcohol that can also be applied to horses.

U.S. Pat. No. 5,032,400 issued in the name of Wiersum et. al. describes a shark liver oil and garlic oil topical analgesic in a cream or ointment base.

None of the prior art particularly describes a topical analgesic for the therapeutic alleviation of sore muscles, bruised ligaments and tendons, lower back pain, arthritis and other similar ailments with a unique blend of essential plant-derived oils.

SUMMARY OF THE INVENTION

In view of the foregoing disadvantages inherent in the prior art, it has been observed that there is need of a therapeutic oil-based composition for topical application to soothe muscular and joint maladies, arthritic symptoms, bruised or strained ligaments and tendons, lower back pain, or other similar ailments.

It has further been observed that there is a need for a composition based on "all-natural" herbal essential oils, plant- and/or vegetable-derived oils, carrier oils, stabilizers, and a fragrance.

The object of the present invention is to provide such a composition in an over-the-counter liquid form.

Another object of the present invention is to provide a composition containing at least a mixture of olive oil, castor oil, grapeseed oil, almond oil, apricot kernel oil, Vitamin E, a stabilizer, one or a mixture of essential oils, and a fragrance within a bottle or similar container.

Yet another object of the invention is to provide an amber or other dark-colored bottle for preventing degradation of the composition within.

Still yet another object of the invention is to provide content-indicating indicia imprinted thereon, embossed thereon, or printed on a label which is subsequently adhered thereto said bottle.

Another object of the invention is to provide a dropper lid insert or other similar flow restrictor, to limit the amount of the preferred composition dispensed onto the user's hands or directly onto the desired area.

Still yet another embodiment of the invention is to provide an aqueous solution of the preferred composition to provide a soaking bath.

To achieve the above and other objectives, the present invention provides for a method of applying the preferred composition topically to the skin of the user, on or about areas that require treatment, or use as a preventative therapeutic oil. To accomplish this, the user applies a small amount of the preferred composition onto their hands or desired area to be subsequently massaged into the skin. Alternatively, the user may produce, if it is not already provided, an aqueous solution of the preferred composition as a liquid soaking bath. The user then massages the composition into the affected or desired area to soothe and repair the skin as well as to provide therapeutic results with its pleasing and calming fragrances.

DETAILED DESCRIPTION OF THE ESSENTIAL COMPOSITION

The best mode for carrying out the invention is presented in terms of its preferred embodiment. However, the invention is not limited to the described embodiment, and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The invention herein refers to an herbal composition, resulting in a liquid topical analgesic for rubbing on one's skin or for use as therapeutic soaking bath. The following formula of oils derived from plant and vegetable sources as well as essential oils therapeutically reduces pain from sore muscles, bruised ligaments and tendons, lower back pain, arthritis, and other similar ailments associated with common aches and pains.

The term "essential oils" herein refers to any concentrated volatile aromatic compound extracted from plants with the general propensity of being hydrophilic.

The term "analgesic" herein refers generally to a chemical compound or composition used to relieve pain.

The term "fragrance" herein refers generally to a chemical compound or composition that naturally emits a pleasing odor.

The term "stabilizer" herein refers generally to a chemical compound or composition that prevents the unwanted chemical reaction between two or more chemical entities.

The term "all-natural" herein refers to components of the present composition that have been extracted or otherwise derived from naturally occurring sources that are unrefined or unprocessed.

The essential composition of the present invention comprises a topical rubbing compound formulated from a variety of plant and vegetable oils and herbal essential oils derived from common sources associated with ayurvedic medicine. The essential composition is a formulation of all-natural products refined to extract their essential oils and remove any extraneous material from the herbs as well as natural oils derived from plants and vegetables.

Typically, the preferred essential composition of the present invention involves the formulaic mixture of essential oils and plant- and/or vegetable-derived oils, with or without a carrier, stabilizer, or fragrance, and at various strengths and volumetric ratios.

An example of a preferred essential composition of the present invention is prepared a follows:

| Component | Amount (Vol %) |
|---|---|
| Castor oil | 19.4 |
| Almond oil | 9.7 |
| Grapeseed oil | 4.8 |
| Apricot kernel oil | 4.8 |
| Vitamin E | 0.2 |
| Stabilizer | 0.2 |
| Olive oil | 58.1 |

-continued

| Component | Amount (Vol %) |
|---|---|
| Fragrance | 0.2 |
| Essential Oil(s) | 2.6 |

| Essential Oils | Amount (Vol %) |
|---|---|
| Tea tree | 30.8 |
| Eucalyptus | 15.4 |
| Sweet birch | 15.4 |
| Ylang ylang | 7.7 |
| Lavender | 15.4 |
| Ginger | 3.8 |
| Red thyme | 3.8 |
| Lemongrass | 7.7 |

The above preferred formula utilizes U.S.-based liquid measurements and the components are commonly found in health care and aromatherapy stores or distributors. The formula is prepared by combining the above components into a vessel as a batch process and mixing well until the composition has reached an adequate concentration of the entire constituents.

Tea tree (*Melaleuca alterniflora*) has well-known antiseptic and antifungal properties and has been used as such for years.

Eucalyptus (*Eucalyptus globulus*), also known as blue gum or Tasmanian blue gum, is typically used in inhalants, embrocations, soaps, gargles, sprays, lozenges and dentrifice, stimulates cognizant activity, and increases concentration under emotional pressure.

Sweet birch (*Betula lenta*), also known as cherry birch or black birch, is typically used medicinally by Native Americans to treat dysentery, diarrhea, soreness, and as a tonic for pain remedies.

Ylang ylang (*Cananga odorata*) is the flower of the cananga tree and is typically used in aromatherapy to relieve high blood pressure and to promote general healing and is used in perfumery as an aphrodisiac.

Lavender (*Lavandula angustifolia*), also known as common lavender, is generally used for its healing and fragrant properties.

Ginger (*Zingiber officinale*), derived from the rhizome of the ginger plant, assists in relieving arthritic symptoms, motion sickness, and inflammation and is an analgesic, antiseptic, and sedative.

Red thyme oil (*Thymus vulgaris, Thymus zygus*, et al.) is an unrectified oil and possesses carminative, expectorant, antimicrobial, and anthelmintic properties.

East-Indian lemongrass or Malabar grass (*Cymbopogon flexuosus*), West-Indian lemongrass (*Cymbopogon citratus*), palmarosa (*Cymbopogon martinii*), and citronella grass (*Cymbopogon nardus* and *Cymbopogon winterianus*) may be used interchangeably in the present composition. Lemongrass is used in aromatherapy for its calming effect to relieve tension and stress and is medicinally used as an antiseptic.

Castor oil (*Ricinus communis*) is a vegetable oil derived from the castor bean that eases constipation and decreases swelling and increases relaxation and circulation.

Almond oil (*Prunus dulcis*), derived from the kernel of either the sweet or bitter almond variety, is typically used in message therapy as an effective emollient.

Grapeseed oil (*Vitis vinifera*) is pressed from the seeds of a variety of grape cultivations and is a by-product of winemaking that is generally used as a sunburn lotion and in message therapy and also as a hand lotion or lip balm.

Apricot kernel oil (*Prunus armeniaca*), pressed from the dried seeds of apricots, acts as a natural emollient that repairs inflamed and damaged skin and is often used in aromatherapy.

Vitamin E, also known as tocopherol, is often used as an overall skin healer and repairing agent.

Olive oil (*Olea europaea*) is a well-known carrier oil and is commonly used to moisturize the skin in topical applications.

The fragrance preferred for the present composition is "Fresh Rain" which adds freshness with a slight floral scent.

The stabilizer preferred for the present composition is germaben II, which is used particularly as an antimicrobial preservative and is highly compatible with most components and compounds found in the cosmetic industry.

An alternate embodiment of the present herbal composition includes the addition of other essential and plant- and/or vegetable-derived oils including: lemon verbena (*Aloysia citriodora*), lemon mint (*Monarda citriodora*), lemon myrtle (*Backhousia citriodora*), chamomile (*Maticaria recutita*), and jojoba (*Simmondsia chinensis*).

Alternate fragrances, stabilizers, and carrier oils may also be utilized within alternate embodiments without modifying or delineating from the therapeutic facilities of the present invention. Also, an aqueous solution of the preferred embodiment may be produced.

The preferred and any alternate embodiments of the present invention are preferably decanted after production into amber or other dark-colored bottles to preserve the contents that are fitted with dropper lid inserts or other similar applicators or with flow restrictors. The bottle should be imprinted, embossed, or fitted with a label with indicia to provide information as to the contents of the bottle.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application and to thereby enable others skilled in the art to best utilize the invention and its various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A formulaic composition of a liquid topical analgesic produced from a blend of plant oils and essential oils that, when applied to a skin surface, will alleviate skin problems and reduce any discomfort associated with common aches and pains, comprising:
   castor oil at 19.4 vol %;
   almond oil at 9.7 vol %;
   grapeseed oil at 4.8 vol %;
   apricot kernel oil at 4.8 vol %;
   vitamin E at 0.2 vol %;
   a stabilizer at 0.2 vol %;
   olive oil at 58.1 vol %;
   a fresh rain odorant at 0.2 vol %;
   and, a blend of essential oils at 2.6 vol %, which blend comprises tea tree oil at 30.8 vol %;
   eucalyptus oil at 15.4 vol %: sweet birch oil at 15.4 vol %; ylang ylang oil at 7.7 vol %;
   lavender oil at 15.4 vol %; ginger oil at 3.8 vol %; red thyme oil at 3.8 vol %; and,
   lemongrass oil at 7.7 vol %.

* * * * *